United States Patent [19]

DeMarco

[11] Patent Number: 5,353,807
[45] Date of Patent: Oct. 11, 1994

[54] MAGNETICALLY GUIDABLE INTUBATION DEVICE

[76] Inventor: Thomas J. DeMarco, 921 Denmeade Walk, Marrietta, Ga. 80064

[21] Appl. No.: 985,670

[22] Filed: Dec. 7, 1992

[51] Int. Cl.$^5$ ............................................. A61B 5/00
[52] U.S. Cl. .................................... 128/772; 128/899
[58] Field of Search ................. 128/653.1, 897–899, 128/772, 200.026, 207.014, 207.015

[56] References Cited

U.S. PATENT DOCUMENTS

| | | | |
|---|---|---|---|
| 3,674,014 | 7/1972 | Tillander | 600/11 |
| 4,173,228 | 11/1979 | Van Steenwyk | 128/653.1 |
| 4,244,362 | 1/1981 | Anderson | 128/772 |
| 4,431,005 | 2/1984 | McCormick | 128/653.1 |
| 5,099,845 | 3/1992 | Besz et al. | 128/653.1 |

*Primary Examiner*—Lee S. Cohen
*Assistant Examiner*—John P. Lacyk
*Attorney, Agent, or Firm*—John J. Daniels

[57] ABSTRACT

A magnetically guidable intubation device including performing means for performing a medical procedure. A magnetically guidable member is connected with a device for performing a medical procedure within the body. The magnetically guidable intubation device is effective to be introduced into a patient's body and magnetically guided within the body by an externally applied magnetic field. A flexible retrieving member may be fixedly attached to the magnetically guidable member and is used for retrieving the magnetically guided member from the body. An external magnetic field is applied and is effective to guide the magnetically guidable member within the body to perform the medical procedure. The magnetically guidable member may include a core and a conductive winding wound around the core. A remotely controllable current source may be provided for applying an electric current to the winding which is effective to induce a magnetic field around the magnetically guidable member. Thus, by changing the field strength and polarity of the magnetic field around the magnetically guidable member, precise control of the magnetically guidable member can be realized.

30 Claims, 10 Drawing Sheets

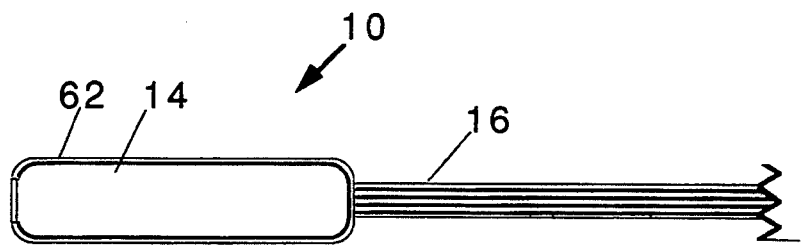
Figure 8(a)
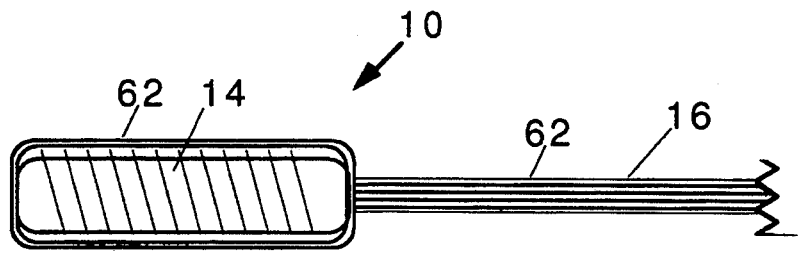
Figure 8(b)
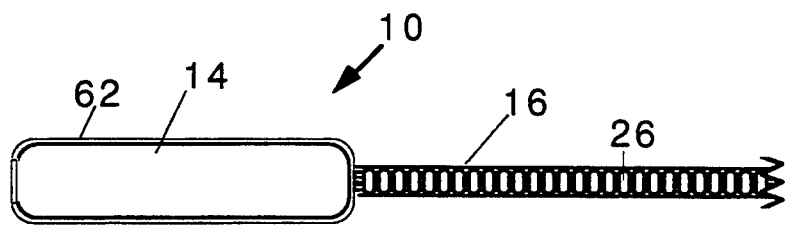
Figure 8(c)
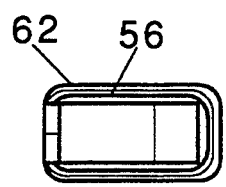 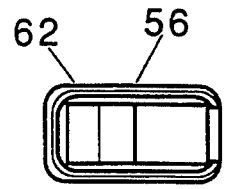
Figure 8(d)   Figure 8(e)

ic device.

MAGNETICALLY GUIDABLE INTUBATION DEVICE

BACKGROUND OF THE INVENTION

The present invention pertains to a magnetically guidable intubation device. More particularly, the present invention pertains to a magnetically guidable intubation device for use in performing medical procedures to an interior of a body; and specifically to performing medical procedures to the large intestine of a human patient.

Conventionally, there are known devices for performing medical procedures within the large intestine of a human patient. A typical device, known as an a colonoscope or endoscope, includes a head disposed at a distal end of an elongated flexible member. The head is inserted into the large intestine of a patient through the rectum and is moved forward through the colon. By manually pushing the elongated flexible member forward, the head is moved through the colon.

The head may be equipped with a diagnostic or therapeutic device. For example, a fiber optic imaging device may be used diagnostically by a doctor for viewing the interior of the large intestine to allow visual inspection for polyps or other malformations of the intestinal wall. The head may also carry a therapeutic tool, such as a remotely controlled cauterizing loop mechanism which is capable of removing, a polyp from the mucosa of the large intestine.

The elongated flexible member typically has a hollow interior which is in communication with an interior chamber of the head. The head holds the therapeutic or diagnostic device. Thus in the case of the fiber optic imaging device, the end of a fiber optic cable bundle and a light source may be contained in the chamber in the head and the fiber optic cable and a power cable for the light source may be enclosed within the flexible elongated member. In the case of the therapeutic device, for example, the cauterizing loop mechanism (known as a polypectomy snare), a cable may be inserted through an operative channel contained within the flexible elongated member so that the cauterizing loop mechanism may be remotely manipulated. At the end of the flexible elongated member opposite the head, an eye piece may be disposed for viewing the interior of the large intestine through the fiber optic cable bundle. Further, a control device may be disposed at the end for manually manipulating, for example, the cauterizing loop mechanism.

In accordance with the conventional art, the elongated flexible member is relatively stiff so that it may effectively push the head forward through the large intestine. Since the large intestine is not straight, but rather has a number of turns to it, it has been difficult to provide an elongated flexible member which has both the stiffness necessary for pushing the head forward through the large intestine and the flexibility to maneuver the head around the various curves of the large intestine. During the procedure, the coventional colonoscope has a tendency to bend into what are known as an alpha loop, N-loop an/or reverse alpha loop. These loops in the colonoscope usually occur in sigmoid colon and further advancement of the colonoscope, if the procedure is not abandoned alltogether, causes great discomfort due to streatching of the colon. Also, in the conventional method, there is the danger of possible complication of colon perforation due to these loops.

To overcome this drawback, a conventional endoscope has been developed which has means for remotely changing the curvature of the elongated flexible member at a portion thereof just below its connection with the head. In this device, the portion of the elongated flexible member capable of being remotely curved is manipulated through a series of cables connected with remotely accessible dials. However, even with this remote curve changing feature of this device, it is still very difficult to maneuver the head comfortably through the turns of the large intestine. In fact, because of the difficulty in maneuvering the head through the convolutions of the large intestine, and the discomfort experienced by the patient, it is common practice for primary care doctors using these generally disclose merely the attachment of a magnetic tip to a semi-rigid tube. These devices generally provide little more than crude positioning of a catheter or intubation device by dragging a permanent magnet across the exterior of the skin to move magnetic tip within an interior cavity of the body such as the throat or stomach.

There is an unsatisfied long felt need to provide a device which can be effectively magnetically guided within the interior of a body to perform a diagnostic and therapeutic medical procedure. In particular, a magnetically guidable intubation device is needed which is easy to use, can be accurately positioned and can be intubated into the large intestine to perform a medical procedure by specialist and nonspecialist.

SUMMARY OF THE INVENTION

The present invention is intended to alleviate the drawbacks of the prior art. In particular, an object of the present invention is to provide an intubation device which results in much less discomfort to a patient as compared with the conventional devices. Another object of the present invention is to provide an intubation device which is easy to use and which is capable of performing medical procedures, such as conventional endoscope to limit its use and thus its effectiveness to the lower end of the large intestine nearest to the rectum, known as the descending colon. An estimated 20 million Americans have colon polyps. Over 150,000 cases of colon cancer are diagnosed each year and this figure is rising. Therefore, there is a great need in the art for a device which may be intubated into the rectum to allow visualization of the entire colon, without causing great discomfort to the patient, which is easily guidable through the intestine and which is capable of performing a variety of therapeutic and diagnostic medical procedures. Such a device should be easy to master by the non-specialist in primary care or technician so as to make colon cancer screening available to a larger number of people.

There have been prior attempts to provide a device which is capable of magnetically guiding a catheter or similar intubated item within a body. Examples of these attempts include U.S. Pat. Nos. 3,961,632, issued to Moosun; 4,077,412, issued to Moosun; 4,249,536, issued to Vega; 4,809,713, issued to Grayzel; 4,671,287, issued to Fiddian-Green; 3,674,014, issued to Tillander; 4,063,561, issued to McKenna; and 4,244,362, issued to Anderson.

However, none of these prior attempts is directed to providing a magnetically guidable intubation device for diagnostic or therapeutic use within the large intestine. Also, these prior attempts are extremely limited in practical use, and imaging of the interior of the body, performing therapeutic measures such as polyp removal, or delivering a medicinal substance to a portion of the interior of the body and the like.

Another object of the present invention is to provide a magnetically guidable intubation device which has a magnetically guidable member which may be introduced into the large intestine of the patient through the rectum and easily and accurately guided through the convolutions of the large intestine by an externally applied magnetic field.

Another object the present invention is to provide such a magnetically guidable member connected with a flexible retrieving member which has at least one externally accessible duct in communication with performing means carried by the magnetically guidable member. Thus, the magnetically guidable member may be guided to a desired portion of the interior of the patient's body to perform a medical procedure using the performing means.

Another object of the present invention is to provide a self-contained magnetically guidable member which carries performing means and which is effective to be introduced in a body and magnetically guided within the body by an externally applied magnetic field to a location of the interior of the body where the performing means can perform a medical procedure. It is a further object of the present invention to provide such a self-contained magnetically guidable member which may be guided and held at a position within the interior of the patient's body so that a substance carried by the magnetically guidable member may be delivered to a selected location within the patient's body.

In accordance with the present invention, a magnetically guidable intubation device is provided. The magnetically guidable intubation device includes performing means for performing a medical procedure. A magnetically guidable member is connected with the performing means and is effective to be introduced into a patient's body and magnetically guided within the body by an externally applied magnetic field. A flexible retrieving member may be fixedly attached to the magnetically guidable member and is used for retrieving the magnetically guided member from the body. This flexible retrieving member may be very limp so as to present minimal resistance to bending. An external magnetic field applying means is further provided for applying the external magnetic field and is effective to guide the magnetically guidable member within the body so that the performing means can perform the medical procedure.

In a preferred embodiment, the magnetically guidable member is configured and dimensioned for insertion through the rectum of a patient's body for performing the medical procedure within the lumen of the large intestine of the patient's body. Preferably the magnetically guidable member has at least one internal chamber for holding the performing means and the flexible retrieving member includes at least one externally accessible duct in communication with the performing means. Through this externally accessible duct, a doctor may manipulate the performing means while performing the medical procedure within the body.

The performing means may include a substance delivering means for delivering a substance to the interior of the body. The performing means may also include therapeutic means for performing a therapeutic medical procedure in the interior of the body. The performing means may also include diagnostic means for performing a diagnostic procedure in the interior of the body, such as imaging means for imaging an interior portion of the body. The imaging means may include a light source and image receiving means such as a fiber optic imaging device, a video camera, or a CCD (charged couple device) camera. In the case of the video camera and the CCD camera, an electronic signal may be produced which may be carried by a wire disposed within the flexible retrieving member or may be transmitted via radio waves or the like to a monitor display so that the doctor performing the medical procedure can see the image. This image may be recorded for later review, or sent to a remote location where a specialist can review the ongoing procedure.

The magnetically guidable member may include a core and a conductive winding disposed around the core. A remotely controllable current source may be provided for applying an electric current to the winding which is effective to induce a magnetic field around the magnetically guidable member. Thus, by changing the field strength and polarity of the magnetic field around the magnetically guidable member, precise control of the magnetically guidable member within the large intestine of the patient can be realized.

In an embodiment of the present invention, a plurality of urging plates are disposed around the flexible retrieving member. The plurality of urging plates are effective to transfer an externally applied urging force to the magnetically guidable member for urging the magnetically guidable head within the interior of the body. In other words, a doctor may urge the urging plate, using an urging knob, so that this force provided by the doctor is transferred through the urging plates to the magnetically guidable head to urge the magnetically guidable head forward through the large intestine. The plurality of urging plates are constructed so that the flexibility of the flexible retrieving member is not hindered. Also, a spring may be disposed between adjacent urging plates to provide a degree of rigidity, while still maintaining the desired ability of the flexible retrieving member to bend around corners, such as the convolutions of the large intestine. Both the magnetically guidable member and the urging plates and/or the retrieving member may be covered by a self-lubricating elastic sheath. Thus, the ease at which the device passes through the interior of the patient's body is increased while the discomfort experienced by the patient is decreased as compared with the conventional art.

Externally positioned detecting means may be provided for detecting the position of the magnetically guidable member as it is being guided through the patient's body. The detecting means may include an x-ray imaging device, an ultrasound imaging device or a magnetic field detecting device. The external magnetic field applying means may include a magnetic field applying plate which comprises at least one individually controllable electromagnetic field source. Each individually controllable electromagnetic field source has a core and an electrically conductive winding. External field controlling means may be provided for controlling a current applied to the electrically conductive winding for controlling the externally applied magnetic field. Further, the magnetic field applying plate may be curved so as to define a space and comprise a plurality of individually controllable electromagnetic sources positioned to apply the externally applied magnetic field within the space. In other embodiments, the external magnetic field applying means may include a single magnetic field source and position controlling means for controlling the position of the magnetic field source, or a magnetic wand.

In another embodiment in accordance with the present invention, a self-contained magnetically guidable member carries the performing means and is effective to be introduced in a body and magnetically guided within the body by an externally applied magnetic field. This self-contained magnetically guidable member does not have a flexible retrieving member, but rather may be small enough so that it can be introduced into the body through the mouth and swallowed to enter the digestive tract. Also, this self-contained magnetically guidable member may be introduce into the body through the rectum, an other orifice of the body or an incision. An external magnetic field applying means applies the external magnetic field which is effective to guide the self-contained magnetically guided member within the body so that the performing means can perform the medical procedure.

The performing means may include imaging means for imaging an interior portion of the body. The imaging means may include image receiving means for receiving an image and generating a signal dependant thereon, and transmitting means for transmitting the signal to a remotely located monitor disposed outside the body for displaying the image.

Further, the performing means may comprise a substance delivering means for delivering a substance to an interior portion of the body and may comprise a chamber for carrying the substance and a substance releasing mechanism for releasing the substance. The substance releasing mechanism may include at least one of a permeable membrane, an exit orifice or a remotely controlled hatch. Thus, in accordance with the present invention, the self-contained magnetically guidable member (or the magnetically guidable member of the other embodiments) may be magnetically guided to a location within the body and held there by an externally applied magnetic field. Then, a medicinal substance may be release so that the substance is effective in treating the particular portion of the interior of the body at which the self-contained magnetically guidable member is held. Thus, such therapeutic medical procedures can be performed without the inconvenience, danger or discomfort of needles, incisions or other invasive procedures. Furthermore, in the case of the self-contained magnetically guidable member, it may be passed from the body through the normal course of digestion, therefore not requiring the flexible retrieving member.

BRIEF DESCRIPTION OF THE DRAWINGS

FIG. 8(a) is a view showing a self-lubricating sheath covering the embodiment of the inventive magnetically guidable intubation device shown in FIG. 1(a);

FIG. 8(b) is a view showing a self-lubricating sheath covering the embodiment of the inventive magnetically guidable intubation device shown in FIG. 1(b);

FIG. 8(c) is a view showing a self-lubricating sheath covering the embodiment of the inventive magnetically guidable intubation device shown in FIG. 2(a);

FIG. 8(d) is a view showing a self-lubricating sheath covering the embodiment of the inventive magnetically guidable intubation device shown in FIG. 6(a);

FIG. 8(e) is a view showing a self-lubricating sheath covering the embodiment of the inventive magnetically guidable intubation device shown in FIG. 6(b);

DETAILED DESCRIPTION OF THE DRAWINGS

Figure 1A:
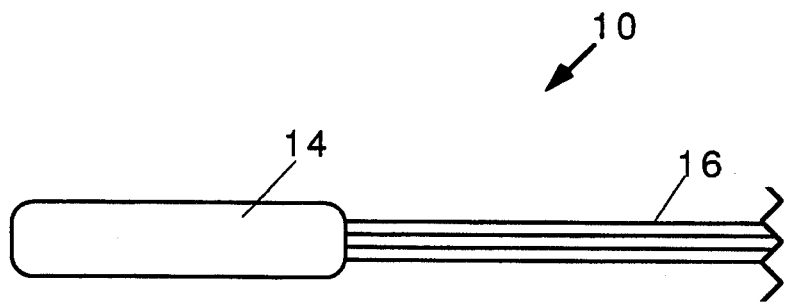
FIG. 1(a) is a view showing an embodiment of the inventive magnetically guidable intubation device.

For purposes of promoting an understanding of the principles of the invention, reference will now be made to the embodiments illustrated in the drawings and specific language will be used to describe the same. It will nevertheless be understood that no limitation of the scope of the invention is thereby intended, there being contemplated such alterations and modifications of the illustrated device, and such further applications of the principles of the invention as disclosed herein, as would normally occur to one skilled in the art to which the invention pertains.

Referring to FIG. 1(a), a description of an embodiment of the inventive magnetically guidable intubation device 10 is given. The inventive magnetically guidable intubation device 10 includes performing means 12 (shown for example, in FIG. 1(c)) for performing a medical procedure. A magnetically guidable member 14 is connected with the performing means 12 and is effective to be introduced into a body and magnetically guided within the body by an externally applied magnetic field (shown for example, in FIG. 5(a)). The magnetically guidable member 14 preferably has a length of 3-4 cm and a diameter of 11-12 mm and may have a neodinium iron boron magnetic substrate. A flexible retrieving member 16 is fixedly attached to the magnetically guidable member 14. This flexible retrieving member 16 is effective for pulling the magnetically guidable member 14 out of the body after the medical procedure has been accomplished. The flexible retrieving member 16 may be a hollow member as discussed below, or may be a solid member comprised of, for example, string, wire or cable or any other suitable flexible material. In accordance with this embodiment of the magnetically guidable intubation device 10, the flexible retrieving member 16 is preferably limp and small enough in diameter so that it offers minimal resistance to the movement of the magnetically guidable member 14 as it is guided through the body. Furthermore, the flexible retrieving member 16 is securely attached to the magnetically guidable member 14 and is sufficiently strong enough to ensure that the magnetically guidable member 14 can be retrieved from within the body by pulling.

In an embodiment of the magnetically guidable intubation device 10, the magnetically guidable member 14 is configured and dimensioned for insertion through the rectum of a human patient so that the performing means 12 are effective for performing a medical procedure within the large intestine. Also, the flexible retrieving member 16 may include at least one externally accessible duct 18 in communication with the performing means 12. The performing means 12 may include at least one of a substance delivering means for delivering a substance to the interior of the body (such as air duct 18 or water duct 18), therapeutic means for preforming a therapeutic medical procedure in the interior of the body (such as a cleaning brush, papollotome, basket, polypectomy snare, forceps, injection needle, catheter, electrode(s), biopsy device, diathermic devices, alligator jaws, scraper, laser, knife or the like). Because of, for example, the looping experienced using conventional devices, poor positioning for therapeutic procedures is often a problem. The present invention provides more precise positioning for biopsy, imaging, polypectomy and other procedures.

Also, the performing means 12 may include diagnostic means for performing a diagnostic procedure in the interior of the body (such as a heat sensor, chemical composition sensor or the like) or imaging means for imaging an interior portion of the body (such as a video camera, fiber optic device, or CCD camera 20). In the case of the video camera or CCD camera 20, an electrical signal may be produced which corresponds to an image which may be transmitted using radio, sound or infrared transmission means, or the signal may be an electrical or light signal transmitted along a conductive wire or fiber optic cable enclosed within the flexible retrieving means. The performing means 12 may also include a suction and/or lens-washing channel.

Figure 1B:
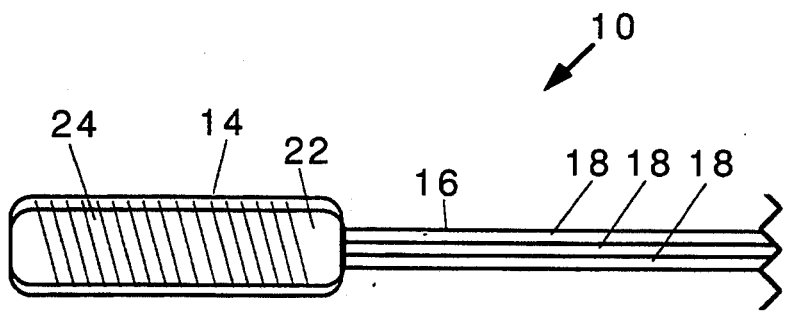
FIG. 1(b) is a view of the embodiment of the inventive magnetically guidable intubation device shown in FIG. 1(a), showing an electrically conductive winding wound around a magnetizable core.
Figure 1C:
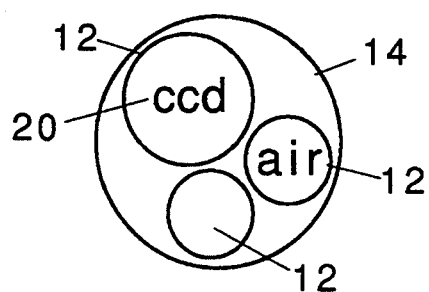
FIG. 1(c) is an enlarged front view of a configuration of an embodiment of the inventive magnetically guidable intubation device.

As shown in FIG. 1(b), the magnetically guidable member 14 may comprise a core 22 having a conductive wiring wound around the core. The core 22 may be a ferromagnetic or a para-magnetic material so that a current carried within the conductive winding 24 induces a magnetic field around the magnetically guidable member 14. A remotely controllable current source may be provided for applying the electrical current to the winding 24 so that the strength and polarity of the magnetic field can be controlled. By controlling the strength and polarity of the magnetic field, movement of the magnetically guidable member 14 within the body can be precisely controlled. Thus, the present invention can precisely position the magnetically guidable member 14 to perform a medical procedure.

Figure 2A:
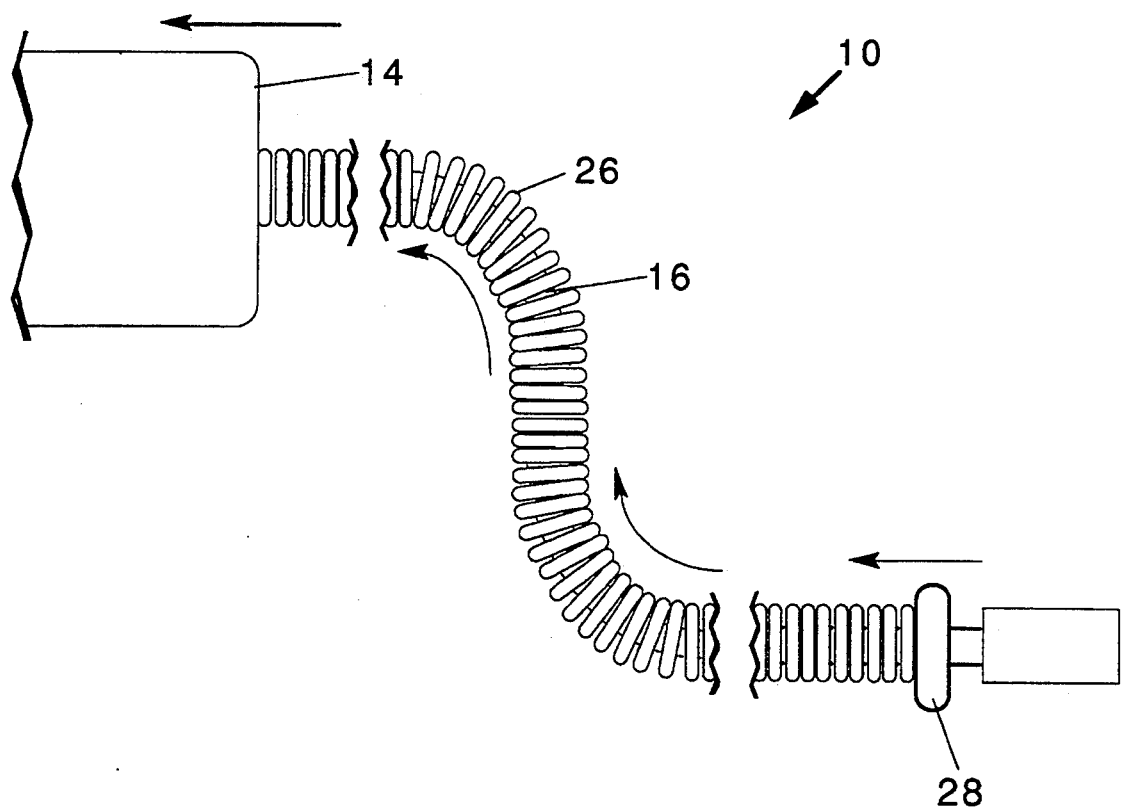
FIG. 2(a) is a partial view of the embodiment of the inventive magnetically guidable intubation device shown in FIG. 1(a) showing a plurality of urging plates disposed around a flexible retrieving member.

Referring now to FIG. 2(a), in accordance with an embodiment of the inventive magnetically guidable intubation device 10, a plurality of urging plates 26 are disposed around the flexible retrieving member 16. The plurality of urging plates 26 are effective to transfer an externally applied urging force to the magnetically guidable member 14 for urging the magnetically guidable member 14 within the interior of the body. In this embodiment, the urging plates 26 provide very little if any restriction to the flexibility of the flexible retrieving member 16. However, when an urging knob 28 is pushed forward any spaces between the adjacent urging plates 26 is compacted until the adjacent plates 26 touch. Any further urging by the urging knob 28 is transmitted along the plurality of urging plates 26 so as to effectively urge the magnetically guidable member 14 forward. However, the plurality of urging plates 26 are effective to transmit the urging force from the urging knob 28 even when the flexible retrieving member 16 is curved, such as when bending around convolutions in the large intestine. Thus, the magnetically guidable head can be urged forward through the large intestine, even around bends, to enhance or substitute for the magnetic attractive force of the externally applied magnetic field.

Figure 2B:
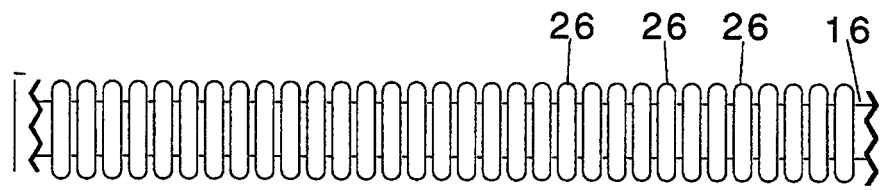
FIG. 2(b) is a partial side view of the plurality of urging plates disposed around the flexible retrieving member shown in FIG. 2(a)
Figure 2C:
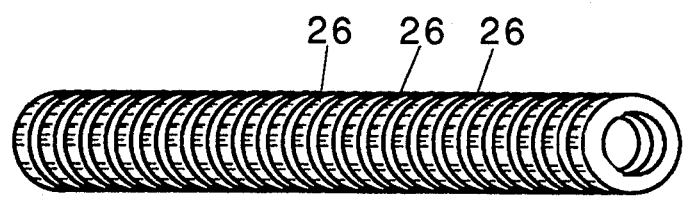
FIG. 2(c) is an isolated perspective view of the urging plates shown in FIG. 2(a)
Figure 2D:
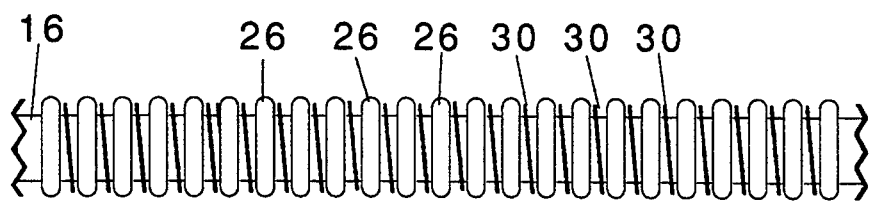
FIG. 2(d) is a partial side view showing the urging plates disposed around the flexible retrieving member shown in FIG. 1(a), further showing springs disposed between the urging plates.

FIG. 2(b), shows the plurality of urging plates 26 in the non-urging position, or in other words, in a position in which the flexible retrieving member 16 is being pulled so as to retrieve the magnetically guidable member 14. FIG. 2(c) is a perspective view showing the plurality of urging plates 26 in the compacted position in which they are effective to transmit the urging force from the urging knob 28 (shown in FIG. 2(a)). As shown in FIG. 2(d), springs 30 may be disposed between the individual urging plates 26 which are effective to impart a degree of rigidity to the flexible retrieving member 16 while still allowing for the bending of the flexible retrieving member 16 as the magnetically guidable member 14 is being guided through the body. These springs 30 may also be effective for maintaining the plurality of urging members at a useful spacing relative to each other.

Figure 3A:
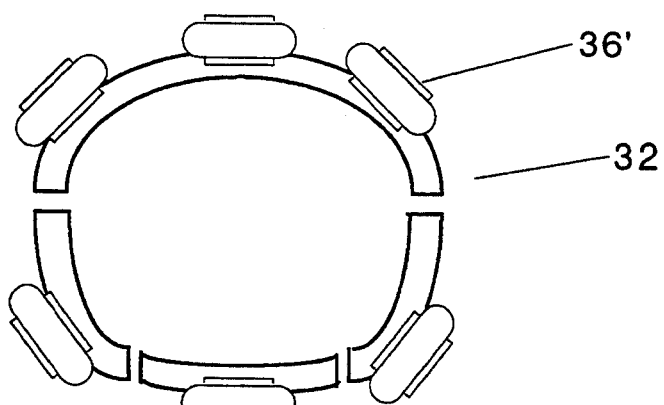
FIG. 3(a) is a cross sectional view of an embodiment of the external magnetic field applying means.
Figure 4A:
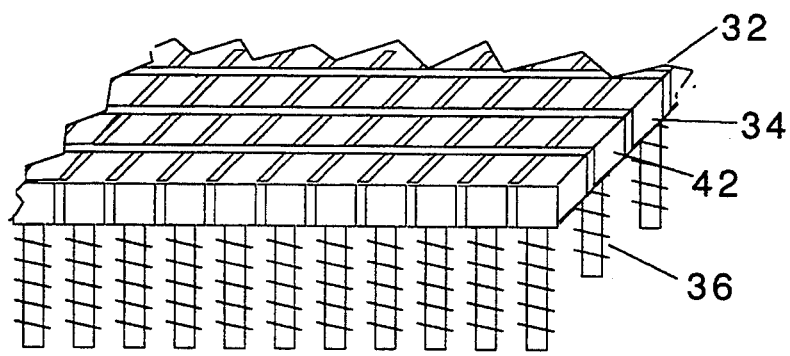
FIG. 4(a) is a perspective cut-away view of a section of an external field applying plate in accordance with the inventive magnetically guidable intubation device.

FIG. 3(a) is a cross sectional view of an embodiment of the external magnetic field applying means 32. The external field applying means may have any suitable shape and configuration. For example, the external magnetic field applying means 32 may have an oval shape as shown, for encompassing a body. The external magnetic field applying means 32 may be one piece, or as described with reference to FIG. 5(c), multiple pieces. The external magnetic field applying means 32 may have one or more relatively large magnetic sources 36', or may comprise a magnetic field plate 34 as described with reference to FIG. 4(a).

Figure 3B:
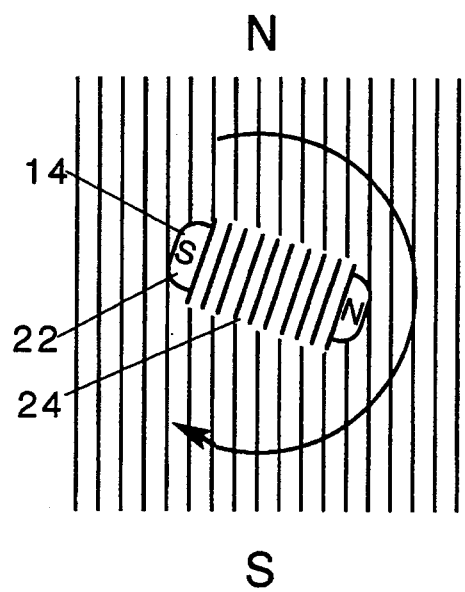
FIG. 3(b) is a schematic drawing showing on isolated view of the magnetically guidable member shown in FIG. 1(b) having an induced magnetic polarity and under the influence of an external magnetic field.

FIG. 3(b) is a schematic drawing showing on isolated view of the magnetically guidable member 14 shown in FIG. 1(b) having an induced magnetic polarity and under the influence of an external magnetic field (shown as parallel lines). The magnetic poles N, S of the magnetically guidable member 14 are urged towards the opposite poles N, S of the magnetic source, thus effecting an induced pivoting of the magnetically guidable member 14 to allow maneuvering. The magnetically guidable member 14 may be an electromagnet so that induced field strength and polarity can be controlled. The control of the magnetic properties of the magnetically guidable member 14, alone or in combination with the control of the external magnetic field, allows positioning and movement of the endoscope within the patient's body.

Figure 3C:
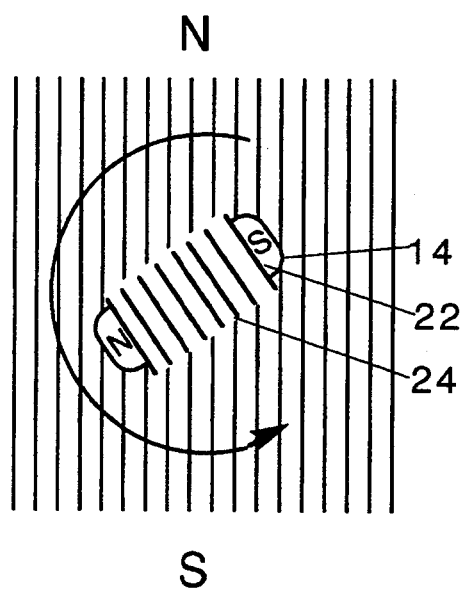
FIG. 3(c) is a schematic drawing showing on isolated view of the magnetically guidable member shown in FIG. 1(b) having a reverse induced magnetic polarity and under the influence of an external magnetic field.

FIG. 3(c) is a schematic drawing showing on isolated view of the magnetically guidable member 14 as shown in FIG. 3(b), but having a reverse induced magnetic polarity. The polarity of the current passing through the winding 24 may be reverse so that the location of the poles N,S may be reversed. As shown, this has the effect of causing the magnetically guidable member 14 to pivot in an opposite direction relative to the direction shown in FIG. 3(b).

Figure 3D:
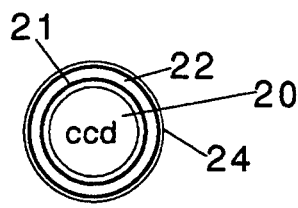
FIG. 3(d) is a cross section of the magnetically guidable member shown in FIG. 1(b), showing a shielded CCD camera.

FIG. 3(d) is a cross section of the magnetically guidable member shown in FIG. 1(b), showing a shielded CCD camera. The magnetically guidable member may be manufactured by boring a through-hole in a core 22 comprised of iron, cobalt, or other suitable metal. A charge-couple device (CCD 20) can be used to obtain video signals. Shielding 21 may be required to combat any interference due to the magnetic field from affecting the video image.

Figure 3E:
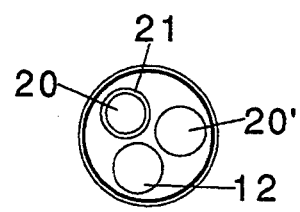
FIG. 3(e) is a cross section of the magnetically guidable member shown in FIG. 1(b), showing a shielded CCD camera, light source and other performing means.

FIG. 3(e) is a cross section of the magnetically guidable member 14 shown in FIG. 1(b), showing a shielded CCD camera 20, light source 20' and other performing means 12. The core 22 may have two or more bores, allowing multiple performing means 12 to be carried by the magnetically guidable member 14. Since positioning of the magnetically guidable member 14 is accomplished through magnetic means, there is no need for a rigid tube to push magnetically guidable member 14 through the patient's large intestine, esophagus or other portion of digestive tract.

In accordance with a preferred embodiment of the present invention, an external magnetic field applying means 32 is provided for applying the external magnetic field which is effective to guide the magnetically guidable member 14 within the body so that the performing means 12 can perform a medical procedure. As shown in 4(a), the external magnetic field applying means 32 may include a magnetic field applying plate 34. The magnetic field applying plate 34 comprises at least one individually controllable electromagnetic field source 36 which has a core 38 and a conductive winding 40. In accordance with this embodiment, the magnetic field applying plate 34 comprises a plurality of such individually controllable electromagnetic field sources 36 which are effective to apply a variable and controllable magnetic field at any selected portion of the magnetic field applying plate 34. Thus, by controlling the individually controllable electromagnetic sources 36, a magnetic field having a desired polarity and strength may be provided at various positions along the magnetic field applying plate 34. The magnetic field may be controlled so as to oscillate, controlled by, for example, a feedback loop, to provide stationary positioning.

Field detectors 42 may also be associated with the magnetic field applying plate 34, or may be disposed separately therefrom. The field detectors 42 detect a position of the magnetically guidable member 14. The field detectors 42 may be comprised of, for example, a winding of electrically conductive material and an amplifier (not shown). As the magnetically guidable member 14, which in this case generates its own magnetic field (as does the embodiment shown in FIG. 1(b)), passes over the individual windings of the field detectors 42, an electrical current is induced in the winding which may be amplified and detected so as to detect the position of the magnetically guidable member 14 relative to the array of field detectors 42.

Figure 5A:
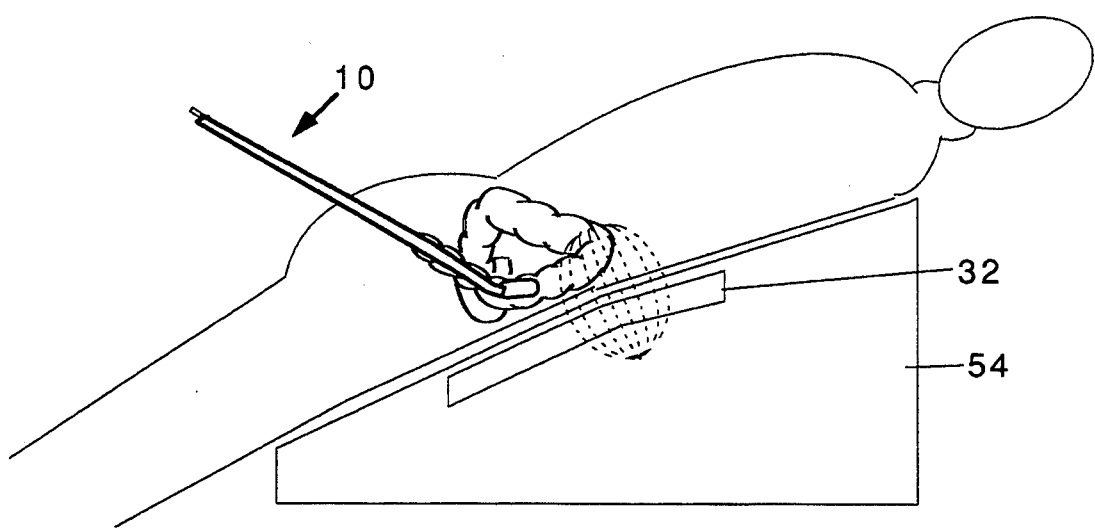
FIG. 5(a) is a schematic view of the embodiment of the inventive magnetically guidable intubation device shown in use.
Figure 5B:
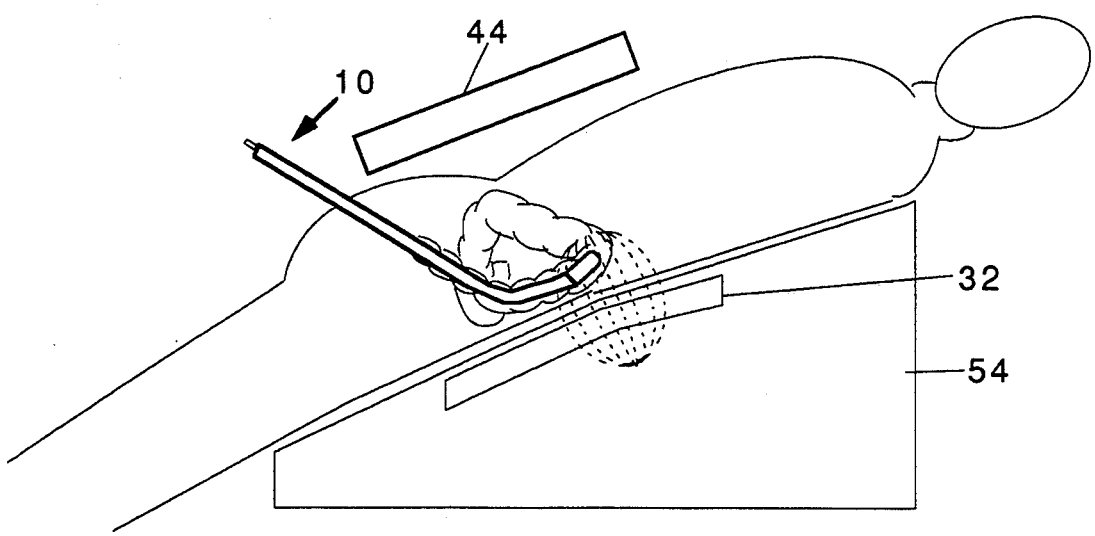
FIG. 5(b) is a schematic view of the embodiment of the inventive magnetically guidable intubation device as shown in FIG. 5(a), being magnetically guided.

Furthermore, externally positioned detecting means 44 (shown in FIG. 5(b)) may be provided for detecting a position of the magnetically guidable member 14. The externally positioned detecting means 44 may comprise an x-ray imaging device, an ultrasound imaging device or the above described magnetic field detectors 42. The material by which the magnetically guidable member 14 is constructed is readily imageable through an x-ray imaging device or an ultrasound imaging device and will contrast sharply with the soft tissue of a body. Alternatively, a tracing element, such as a barium compound may be utilized to enhance the contrast, to thus make the magnetically guidable member 14 particularly suited for such imaging.

Figure 4B:
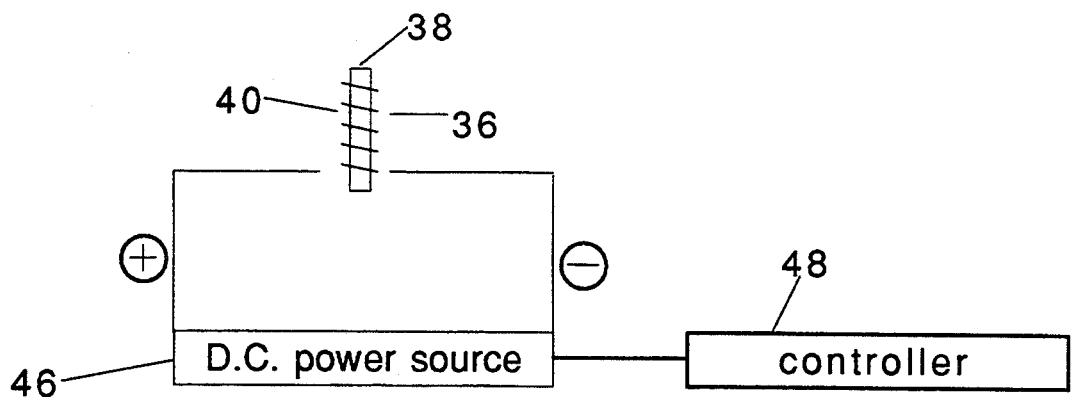
FIG. 4(b) is an isolated view of an individually controllable electromagnetic source shown in FIG. 4(a)

A shown in FIG. 4(b), the individually controllable electromagnetic sources 36 are comprised of a core 38, which may be a ferromagnetic, para-magnetic of other suitable material, around which a winding 40 of an electrically conductive material (such as copper wire, conductive polymer strands or the like) is wound. A current applied by a power source 46 (in this case a DC power source 46, which may alternatively be an AC power source) flows through the winding 40, magnetizing the core 38, thus inducing a magnetic field. The strength and polarity of the current flowing through the winding 40 may be controlled by a controller 48. Furthermore, the controller 48 may be controlled through instructions given by a microprocessor. In addition, the microprocessor may receive input corresponding to the position of the magnetically guidable member 14 detected by the externally positioned detecting means 44 or the field detectors 34 so as to effect automatic or semi-automatic control of the individually controllable electromagnetic sources 36 and thus control of externally applied magnetic field guiding the magnetically guidable member 14.

Figures 4C, 4D:
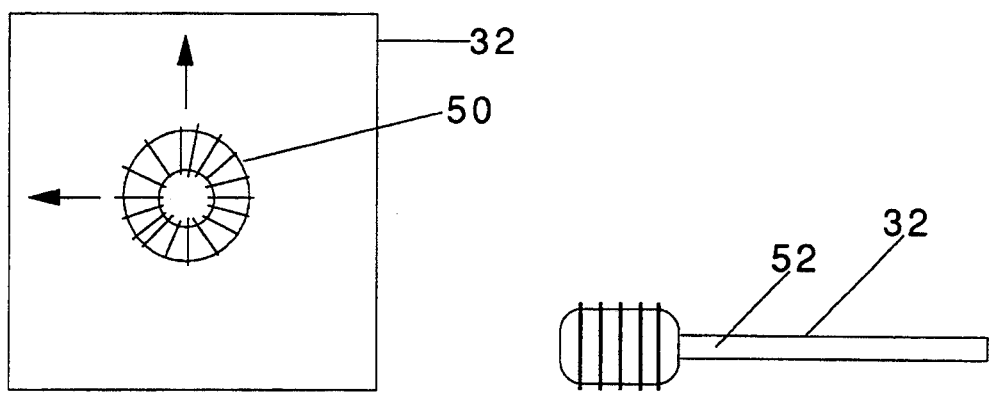
FIG. 4(c) is a schematic view showing an alternative external magnetic field applying plate.
FIG. 4(d) is a schematic view showing an other alternative external magnetic field applying means.

As shown in FIG. 4(c), the external magnetic field applying means 32 may include a magnetic field source, such as a single magnetic field source 50 which may be an electromagnet or a permanent magnet. This single magnetic field source 50 is movable within a range effective to move the externally applied magnetic field so as to magnetically guide the magnetically guidable body to desired positions within the body. In the case of the magnetic field source being an electromagnetic field source, the strength and polarity of the magnetic field may also be varied to further manipulate the magnetically guidable member 14 within the body.

Position controlling means (shown schematically as arrows) may be provided for controlling the position of the single magnetic field source 50. The position controlling means may include cables or rods for moving the magnetic field source about at least an x-axis and/or a y-axis to effect the movement of the externally applied magnetic field. Also, the position controlling means may be under the control of instructions provided by a microprocessor so as to automatically or semi-automatically position the magnetically guidable member 14 within the body.

As shown in FIG. 4(d), an alternative external magnetic field applying means 32 may be comprised of a hand-carried-and-operated external magnetic field applying wand 52. This external magnetic field applying wand 52 may be a permanent or electromagnet by which a doctor or technician may guide the magnetically guidable member 14 within the body. In the case of the hand-carried-and-operated external field applying wand 52 being an electromagnet, the polarity and strength of the externally applied magnetic field may be selectively varied.

Referring now to FIG. 5(a) and 5(b), the use of an embodiment of the inventive magnetically guidable intubation device 10 will be described. As shown in FIG. 5(a), a patient is disposed in a reclined position on a support 54. Alternatively, the patient may lay flat on his or her stomach, in which case, the support 54 and field applying means 32 may also be flat. When the inventive magnetically guidable intubation device 10 is used for performing medical procedures within the large intestine, it is preferable that the shape of the support 54 position the patient such that the external magnetic field applying means 32 is most effective for guiding the magnetically guidable intubation device 10. In other words, as shown in FIGS. 5(a) and 5(b), the region of the patient's body having the large intestine is disposed close to the external magnetic field applying means 32.

As shown in FIG. 5(a), the magnetically guidable member 14 is introduced into the large intestine of the patient through the patient's rectum. A magnetic field (shown in dashed-lines) applied by the external magnetic field applying plate 34 repels and/or attracts the magnetically guidable member 14 so as to guide it through the convolutions of the large intestine. Furthermore, to help in urging the magnetically guidable member 14 forward through the large intestine, and in particular to urge the magnetically guidable member 14 through the large intestine at positions where the externally applied magnetic field is relatively weak (such as at portions of the large intestine which are furthest from the external magnetic field applying plate 34) the urging plates 26 are utilized.

The doctor or technician urges forward the urging knob 28 which causes any space between the individual urging plates 26 to contract until adjacent urging plates 26 are touching and are effective to transmit the urging force forward through the plurality of urging plates 26 to the magnetically guidable member 14 to urge the magnetically guidable member 14 along through the large intestine. When the magnetically guidable member 14 comes to a bend in the large intestine, the urging plates 26 allow the flexible conduit to curve around this bend while still providing the forward urging force to the magnetically guidable member 14. Thus, as shown in FIG. 5(b), the magnetically guidable member 14 is urged along until the externally applied magnetic field becomes effective for guiding the magnetically guidable member 14. Further, a first magnetically guidable member 14 may be introduced for visual inspection of the large intestine. Then, a second magnetically guidable member (not shown) may be introduced which is effective to perform a medical procedure, such as polyp removal from the mucosa of the large intestine.

Figure 5C:
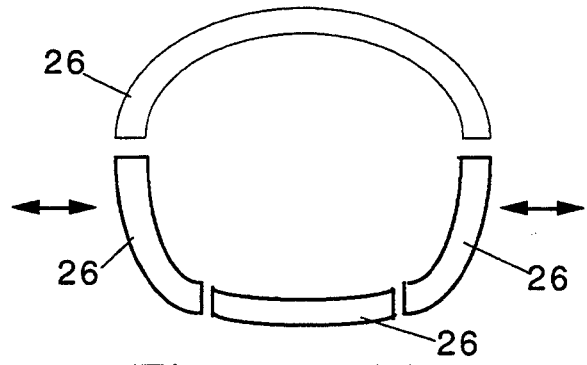
FIG. 5(c) is a sectional view of an alternative configuration of the external magnetic field applying plate.

As shown in FIG. 5(c), the external magnetic field applying means 32 may be composed of a plurality of plates 26 some of which may be curved, which are moveable in the relative positions to accommodate different sized patients, and which are effective to apply the externally applied magnetic field to appropriate locations of the patients body to magnetically guide the magnetically guidable member 14. Also, the patient may be reoriented during the intubation procedure so that the applied externally applied magnetic field is most effective at guiding the magnetically guidable member 14.

Figure 6A:
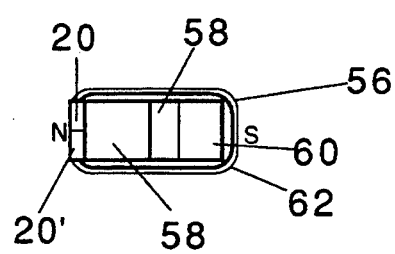
FIG. 6(a) is schematic view of another embodiment of the inventive magnetically guidable intubation device.
Figure 6B:
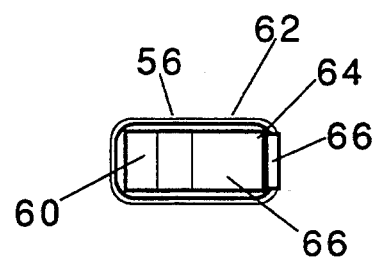
FIG. 6(b) is a schematic view of another configuration of the embodiment of the inventive magnetically guidable intubation device shown in FIG. 6(a)

Referring now to FIGS. 6(a) and 6(b), another embodiment of the inventive magnetically guidable intubation device 10 is shown. In this embodiment, performing means 12 are provided for performing a medical procedure. A self-contained magnetically guidable member 56 is provided and is connected with the performing means 12. In this description, and in the claims, the self-contained magnetically guidable member 56 is a magnetically guidable member for intubation into the interior of a body, which is not physically connected with the outside of the body through any means, such as the above described flexible retrieving means 16 or the like. In other words, the self-contained magnetically guidable member 56 is free to move within the body, without the restriction of a long "tail" member. This embodiment of the self-contained magnetically guidable member 56 may be introduced into the body through the mouth, such as by swallowing or through any other orifice or incision made in the body. Thus, this self-contained magnetically guidable member 56 does not have its movement restricted by any elongated flexible member such as the flexible retrieving member 16 described above with reference to the other embodiments.

The inventive self-contained magnetically guidable member 56 is guidable within the body by an externally applied magnetic field. An external magnetic field applying means 32 is provided for applying the external magnetic field which is effective to guide the magnetically guidable member 14 within the body so that the performing means 12 can perform the medical procedure. The performing means 12 may include imaging means for imaging an interior portion of the body which comprises an image receiving means, such as a CCD camera 20, for receiving an image and generating a signal dependent thereon. Transmitting means 58 may be provided for transmitting the signal to a monitor for displaying the image.

Thus, as shown in FIG. 6(a), the self-contained magnetically guidable member 56 may be comprised of a hollow permanent magnetic cylinder having a north pole and a south pole. A CCD camera 20 and light source 20' may be disposed at one end of the permanent magnet cylinder and imaging electronics and transmitting means 58 may be provided within the interior. Receiving electronics 58' may be provided for receiving remote signals for remotely controlling the self-contained magnetically guidable member 56 so that, for example, the light source 20' can be turned on or transmission of the signal can be started remotely. Furthermore, the self-contained magnetically guidable member 56 may include a winding (not shown) of electrically conductive material around a magnetizable core and a battery 60 for supplying a current to the winding. Thus, the polarity and field strength of the self-contained magnetically guidable member 56 may be remotely controlled by control signals transmitted from an external source and received by receiving electronics contained within the self-contained magnetically guidable member 56. Also, an elastic sheath 62 may be disposed covering the self-contained magnetically guidable member 56 and the elastic sheath 62 may be self-lubricating.

As shown in FIG. 6(b), the performing means 12 carried by the self-contained magnetically guidable member 56 may comprise a substance delivering means 64 for delivering a substance 66' to an interior portion of the body, and may comprise a chamber for carrying a substance and a substance releasing mechanism 66 for releasing the substance 66'. The substance releasing mechanism 66 may include at least one of a permeable membrane, an exit orifice or a remotely controlled hatch. Thus, in accordance with the present invention, the self-contained magnetically guidable member 56 may be introduced into the body either orally or through the rectum and magnetically guided to a predetermined position within the interior of the body.

By maintaining a steady externally applied magnetic field, the self-contained magnetically guidable member 56 may be held in place so that a substance 66' (such as medicine for chemotherapy), can be held at the site of delivery and slowly released. It is particularly noted that the metallic structure of the self-contained magnetically guidable member 56 makes x-ray or ultrasound imaging clear so that it is easy to check for precise placement. Thus, the inventive self-contained magnetically guidable member 56 allows for localized delivery of medicine without requiring an invasive procedure.

The remotely releasable hatch may be operated by a magnetic field. In this case, the magnetic field required to position the self-contained magnetically guidable member 56 should be less than that required to open the hatch. Once the self-contained magnetically guidable member 56 is in position, a stronger magnetic field may be applied which is effective to open the hatch thereby releasing the substance 66' at the desired location.

Figure 7A:
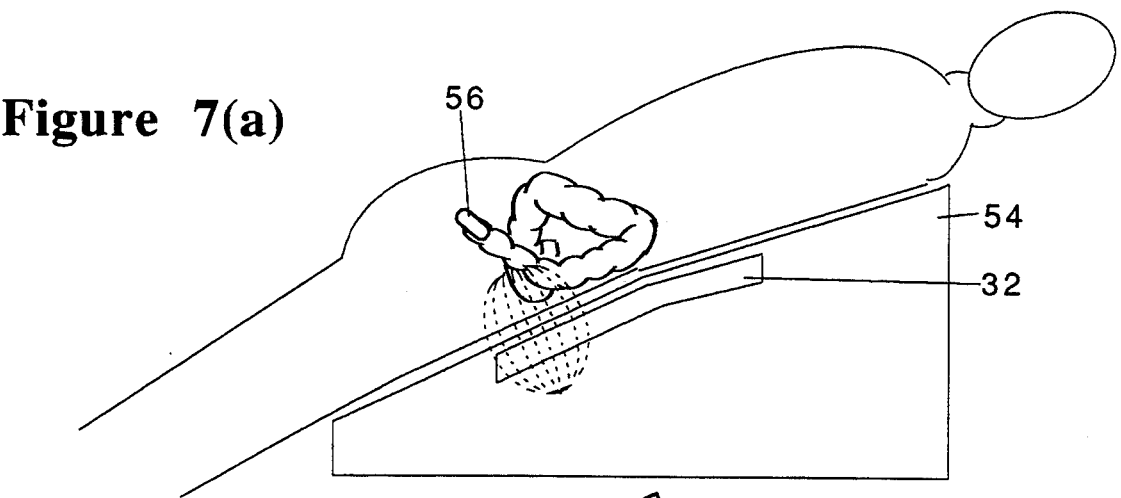
FIG. 7(a) is a schematic view of the embodiment of the inventive magnetically guidable intubation device shown in FIG. 6(a) shown in use.
Figure 7B:
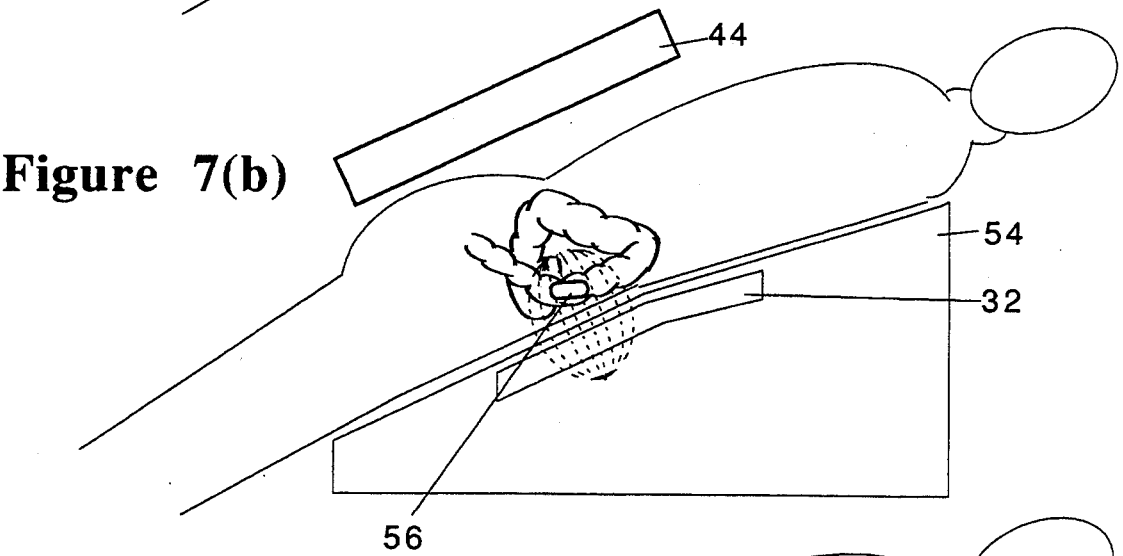
FIG. 7(b) is a schematic view of the embodiment of the inventive magnetically guidable intubation device as shown in FIG. 7(a) being magnetically guided and further showing detecting means.
Figure 7C:
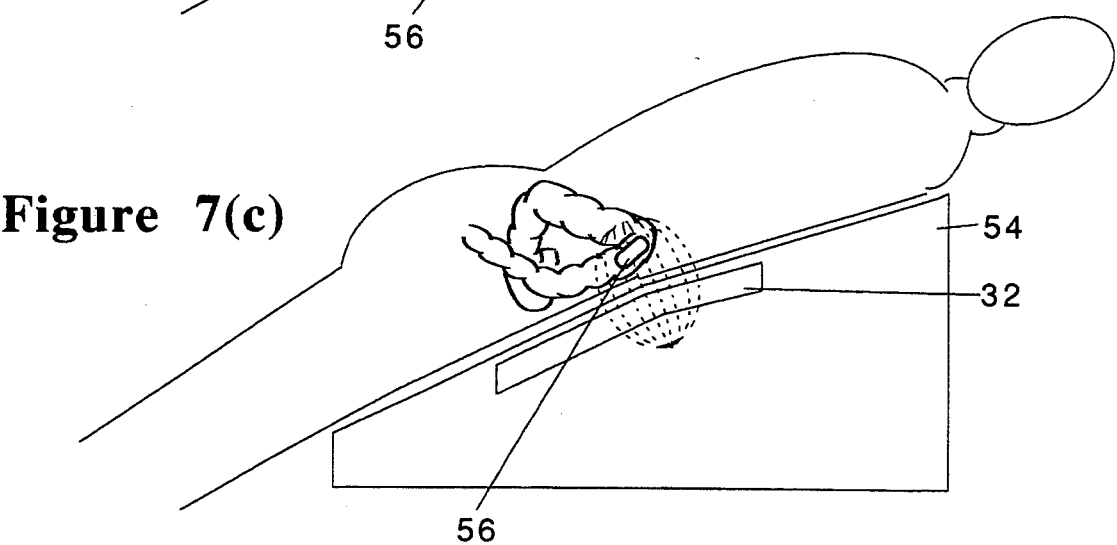
FIG. 7(c) is a schematic view of the embodiment of the inventive magnetically guidable intubation device shown in FIG. 7(a), showing the magnetically guidable member held at a position by an externally applied magnetic field.

Referring now to FIGS. 7(a)-7(c), the medicinal use of the inventive self-contained magnetically guidable member 56 will be described. The patient is first positioned on the support 54 as has been described above with reference to FIG. 5(a). The self-contained magnetically guidable member 56 may be introduced into the large intestine of the patient through the rectum. By controlling the strength and polarity of the externally applied magnetic field applied through the external magnetic field applying means 32, the self-contained magnetically guidable member 56 is guided through the large intestine. Since the elastic sheath 62 covering the self-contained magnetically guidable member 56 may be self-lubricating, the self-contained magnetically guidable member 56 smoothly moves along through the large intestine guided by the externally applied magnetic field.

As shown in FIG. 7(b), detecting means, such as an x-ray device, ultrasound device or field detecting means may be used so that the position of the magnetically guidable member 14 may be determined. Alternatively, the self-contained magnetically guidable member 56 may be introduced into the body through the mouth by swallowing, passed through the stomach, through the small intestine and into the large intestine until it reaches a desired location (shown in FIG. 7(b)). Once the self-contained magnetically guidable member 56 is detected at the desired location, a magnetic field may be externally applied to hold the self-contained magnetically guidable member 56 at this position for delivery of medicine, imaging, or other therapeutic or diagnostic procedures. An externally applied magnetic field source may be carried by the patient so that the patient's mobility is less restricted while medicine is being delivered to a location within the patient's body. Further, means may be provided by which the hatch remains opened only while the self-contained magnetically guidable member 56 is within the externally applied magnetic field. Thus, if the self-contained magnetically guidable member 56 becomes dislodged, it will not continue to deliver the substance at a wrong location.

Referring to FIGS. 8(a)-8(d), the various embodiments of the inventive magnetically guided intubation device are shown. FIG. 8(a) shows the embodiment shown in FIG. 1(a), further having an elastic sheath 62 covering the magnetically guidable member 14 and the flexible retrieving member 16. In any of the embodiments, the elastic sheath 62 may be self-lubricating, as described below with reference to FIG. 9(a)-9(d). FIG. 8(b) shows the embodiment shown in FIG. 1(b), further having an elastic sheath 62 covering the winding 24 and core 22 of the magnetically guidable member 14 and also covering the flexible retrieving member 16. FIG. 8(c) shows the embodiment shown in FIG. 6(a), further having an elastic sheath 62 covering the self-contained magnetically guidable member 56, and FIG. 8(d) shows the embodiment shown in FIG. 6(b), further having an elastic sheath 62 covering the self-contained magnetically guidable member 56.

Figure 9A:
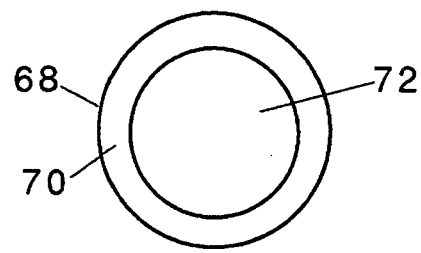
FIG. 9(a) Is a schematic view of a microcapsule used for self-lubrication of the self-lubricating sheath.

Referring to FIGS. 9(a)–9(d), embodiments of the self-lubricating elastic sheath will be described. As shown in FIG. 9(a), a self-lubricating microcapsule 68 may be formulated having a water soluble outer shell 70 encapsulating a water soluble lubricating inner phase 72. The water soluble outer shell 70 may be, for example, a gelatine, polymer or other suitable material capable of forming a microcapsule 68. The internal phase 72 may be a glycerine, an organic lubricant or an inorganic lubricant. It is noted that preferably the outer shell 70 and the inner phase 72 are made of water soluble material. However, this is not necessarily so. Other materials, such as petroleum jelly, or other oil based lubricants may be used.

Figure 9B:
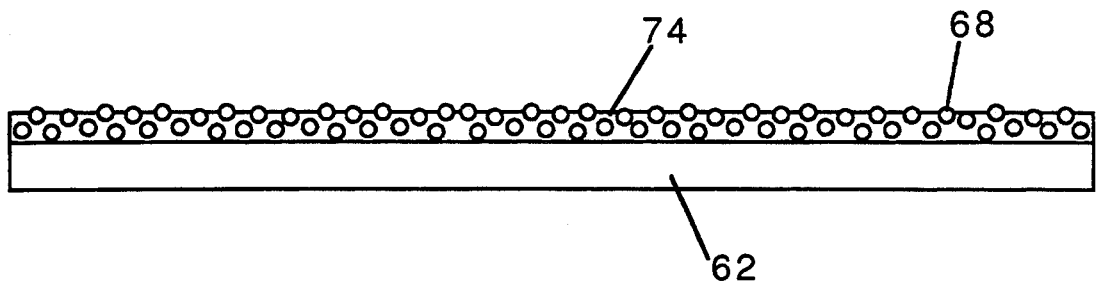
FIG. 9(b) is a schematic representation showing a structure of the self-lubricating sheath having the microcapsules shown in FIG. 9(a) embedded within a binder.

As shown in FIG. 9(b), the elastic sheath 62 may be comprised of an elastic material, such as latex, other polymer, synthetic rubber, natural rubber or other suitable flexible material. It is noted that it is desirable that the sheath 62 be elastic but this is not necessarily so, and an inelastic material such as vinyl, polyurethane or the like may be used. A binder 74, which may be a gum based material, or other suitable material, may have the self-lubricating microcapsules 68 dispersed therein. This binder 74 and the microcapsule 68 mixture is coated on the exterior of the elastic sheath 62. By selecting materials having appropriate solubility in water, it is possible to design a self-lubricating elastic sheath 62 which continually provides lubrication to the inventive magnetically guided intubation device 10 while it is being inserted and while it is in the patient's body.

Figure 9C:
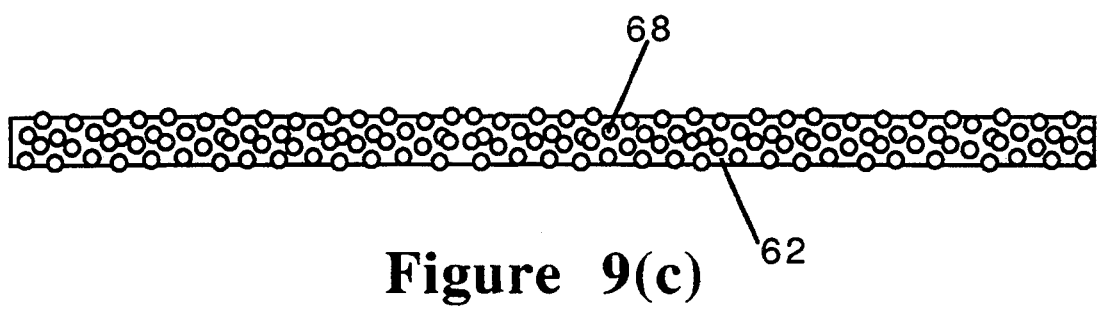
FIG. 9(c) is a schematic representation of the self-lubricating sheath showing the microcapsule shown in FIG. 9(a) embedded within a matrix comprising the self-lubricating sheath.

As shown in FIG. 9(c), the elastic sheath 62 may be comprised of a binding matrix such as latex, gum based material or other suitable material in which is dispersed the self-lubricating microcapsules 68. Thus, throughout the procedure the matrix and self-lubricating microcapsule 68 will be continually worn away layer by layer so that a fresh layer, and thus continual lubrication is provided.

Figure 9D:
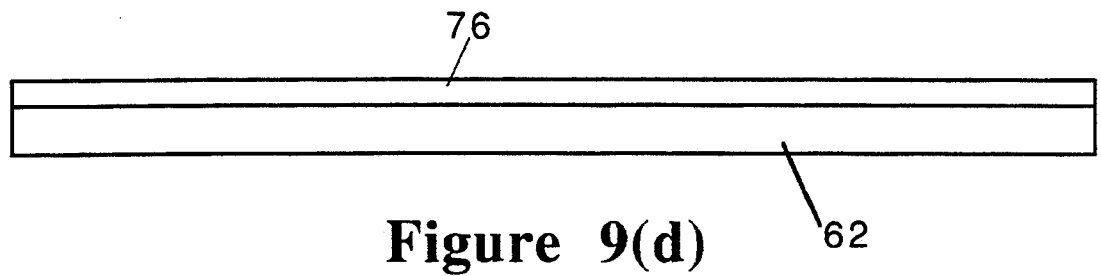
FIG. 9(d) is a schematic representation showing an embodiment of the self-lubricating sheath having a soluble self-lubricating coating.

Finally, as shown in FIG. 9(d), the self-lubricating feature of the elastic sheath 62 may be accomplished by applying a lubricating coating 76 over the elastic sheath 62. This lubricating coating 76 may have a dry form which is water activated to produce a continuous lubricating slime throughout the medical procedure. Thus, in accordance with the present inventive magnetically guidable intubation device 10, continuous lubrication is provided to the magnetically guidable member 14 and the flexible retrieving member 16 throughout the procedure, thus further providing for the comfort of the patient and the ease of maneuverability of the inventive magnetically guidable intubation device 10 within the interior of the body.

With respect to the above description, it is realized that the optimum dimensional relationships for parts of the invention, including variations in size, materials, shape, form, function, and manner of operation, assembly and use, are deemed readily apparent and obvious to one skilled in the art. All equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to, falling within the scope of the invention.

I claim:

1. A magnetically guidable intubation device, comprising: performing means for performing a medical procedure; a magnetically guidable member connected with the performing means and effective to be introduced into a body and magnetically guided within the body by an externally applied magnetic field; a flexible retrieving member fixedly attached to the magnetically guidable member; an external magnetic field applying means for applying the external magnetic field effective to guide the magnetically guidable member within the body so that the performing means can perform the medical procedure; and a plurality of urging plates each disposed around the flexible retrieving member, the plurality of urging plates effective to transfer an externally applied urging force to the magnetically guidable head for urging the magnetically guidable head within the interior of the body.

2. A magnetically guidable intubation device according to claim 1; wherein the magnetically guidable member includes at least one internal chamber for holding the performing means; and wherein the flexible retrieving member includes at least one externally accessible duct in communication with the performing means.

3. A magnetically guidable intubation device according to claim 1; wherein the performing means includes at least one of substance delivering means for delivering a substance to the interior of the body, therapeutic means for performing a therapeutic medical procedure in the interior of the body, diagnostic means for performing a diagnostic procedure in the interior of the body and imaging means for imaging an interior portion of the body, the imaging means comprising at least one of a fiber optic member, a video camera and a CCD camera, the video camera and the CCD camera effective to produce a signal corresponding to an image for display on a monitor positioned outside the body.

4. A magnetically guidable intubation device according to claim 3; wherein the magnetically guidable member includes at least one internal chamber for holding the performing means; and wherein the flexible retrieving member includes at least one externally accessible duct in communication with the performing means.

5. A magnetically guidable intubation device according to claim 1; wherein the magnetically guidable member further comprises a core and a conductive winding wound around the core; and further comprising a remotely controllable current source for applying an electric current to the winding effective to induce a magnetic field around the magnetically guidable member.

6. A magnetically guidable intubation device according to claim 1; further comprising at least one spring member disposed between at least two adjacent urging plates.

7. A magnetically guidable intubation device according to claim 1; further comprising a sheath covering at least one of at least a portion of the magnetically guidable member and at least a portion of the plurality of urging plates.

8. A magnetically guidable intubation device according to claim 7, wherein the sheath is self-lubricating.

9. A magnetically guidable intubation device according to claim 1; further comprising externally positioned detecting means for detecting a position of the magnetically guidable member and generating a detection signal in response thereto, the detecting means comprising at least one of an x-ray imaging device, an ultrasound imaging device and a magnetic field detecting device.

10. A magnetically guidable intubation device according to claim 1; wherein the external magnetic field applying means includes an electro-magnetic field source; and controlling means for controlling the position of the magnetic field produced by the electromagnetic field source and for controlling the magnetic field strength of the magnetic field produced by the electromagnetic field source to magnetically guide the magnetically guidable member within the body.

11. A magnetically guidable intubation device, comprising: performing means for performing a medical procedure; a magnetically guidable member connected with the performing means and effective to be introduced into a body and magnetically guided within the body by an externally applied magnetic field; a flexible retrieving member attached to the magnetically guidable member; an external magnetic field applying means for applying the external magnetic field effective to guide the magnetically guidable member within the body so that the performing means can perform the medical procedure, the external magnetic field applying means including a magnetic field applying plate comprising at least one individually controllable electromagnetic field source having a core and an electrically conductive winding, and external field controlling means for controlling a current applied to the electrically conductive winding for controlling the externally applied magnetic field.

12. A magnetically guidable intubation device according to claim 11; wherein the magnetic field applying plate is curved so as to form a space to receive a portion of a body in which the magnetically guided member is guided, and comprises a plurality of individually controllable electromagnetic sources positioned to apply the externally applied magnetic field within the space.

13. A magnetically guidable intubation device according to claim 11; wherein the magnetically guidable member includes at least one internal chamber for holding the performing means; and wherein the flexible retrieving member includes at least one externally accessible duct in communication with the performing means.

14. A magnetically guidable intubation device according to claim 11; wherein the performing means includes at least one of substance delivering means for delivering a substance to the interior of the body, therapeutic means for performing a therapeutic medical procedure in the interior of the body, diagnostic means for performing a diagnostic procedure in the interior of the body and imaging means for imaging an interior portion of the body, the imaging means comprising at least one of a fiber optic member, a video camera and a CCD camera to produce a signal corresponding to an image for display on a monitor positioned outside the body.

15. A magnetically guidable intubation device according to claim 14; wherein the magnetically guidable member includes at least one internal chamber for holding the performing means; and wherein the flexible retrieving member includes at least one externally accessible duct in communication with the performing means.

16. A magnetically guidable intubation device according to claim 11; wherein the magnetically guidable member further comprises a core and a conductive winding wound around the core; and further comprising a remotely controllable current source for applying an electric current to the winding effective to induce a magnetic field around the magnetically guidable member.

17. A magnetically guidable intubation device according to claim 11; further comprising externally positioned detecting means for detecting a position of the magnetically guidable member and generating a detection signal in response thereto.

18. A magnetically guidable intubation device, comprising: performing means for performing a medical procedure having a substance delivering means for delivering a substance to an interior portion of a body and comprising a chamber for carrying a substance and a substance releasing mechanism for releasing the substance; a self-contained magnetically guidable member connected with the performing means and effective to be introduced into a body and magnetically guided within the body by an externally applied magnetic field; and external magnetic field applying means for applying the external magnetic field effective to guide the magnetically guidable member within the body so that the performing means can perform the medical procedure.

19. A magnetically guidable intubation device according to claim 18; wherein the performing means comprising imaging means for imaging an interior portion of the body comprising image receiving means for receiving an image and generating a signal dependent thereon and transmitting means for transmitting the signal to a monitor disposed outside the body for displaying the image.

20. A magnetically guidable intubation device according to claim 18; wherein the substance releasing mechanism includes at least one of a permeable membrane, an exit orifice and a remotely controlled hatch.

21. A magnetically guidable intubation device according to claim 20; wherein the substance releasing mechanism includes means for releasing the substance in response to an externally applied magnetic field.

22. A magnetically guidable intubation device according to claim 18; wherein the external magnetic field applying means includes a magnetic field applying plate comprising at least one individually controllable electromagnetic field source, and external field controlling means for controlling the externally applied magnetic field.

23. A magnetically guidable medical device for use within the large intestine of a human body comprising: performing means for performing a medical procedure; and magnetic guiding means comprising a magnetically guidable member connected with the performing means and effective to be introduced into a the large intestine through the rectum of the human and magnetically guided within the large intestine by an externally applied magnetic field, an external magnetic field applying means for applying the external magnetic field effective to guide the magnetically guidable member within the body so that the performing means can perform the medical procedure, wherein at least one of the magnetically guidable member and the external magnetic field applying means comprises a variable electromagnetic field source, and external field controlling means for controlling a current applied to the variable electromagnetic field source.

24. A magnetically guidable intubation device according to claim 23; wherein the magnetically guidable member comprises a core and a conductive winding wound around the core; and further comprising a remotely controllable current source for applying an electric current to the winding effective to induce a magnetic field around the magnetically guidable member.

25. A magnetically guidable intubation device according to claim 23; wherein the external magnetic field applying means includes a magnetic field applying plate comprising at least one individually controllable electromagnetic field source having a core and an electrically conductive winding, and the external field controlling means including means for controlling a current applied to the electrically conductive winding for controlling the externally applied magnetic field.

26. A magnetically guidable intubation device according to claim 23; wherein the magnetically guidable member includes at least one internal chamber for holding the performing means: and further comprising a flexible retrieving member attached to the magnetically guidable member for retrieving the magnetically guidable member from the intestine and having at least one externally accessible duct in communication with the performing means.

27. A magnetically guidable intubation device according to claim 23; wherein the performing means includes at least one of substance delivering means for delivering a substance to the interior of the body, therapeutic means for performing a therapeutic medical procedure in the interior of the body, diagnostic means for performing a diagnostic procedure in the interior of the body and imaging means for imaging an interior portion of the body, the imaging means comprising at least one of a fiber optic member, a video camera and a CCD camera to produce a signal corresponding to an image for display on a monitor positioned outside the body.

28. A magnetically guidable intubation device according to claim 23; further comprising externally positioned detecting means for detecting a position of the magnetically guidable member and generating a detection signal in response thereto.

29. A magnetically guidable intubation device according to claim 23; wherein the performing means comprises a substance delivering means for delivering the substance to an interior portion of the body comprising a chamber for carrying a substance and a substance releasing mechanism for releasing the substance.

30. A magnetically guidable intubation device according to claim 29; wherein the substance releasing mechanism includes at least one of a permeable membrane, an exit orifice and a remotely controlled hatch.

* * * * *

UNITED STATES PATENT AND TRADEMARK OFFICE
CERTIFICATE OF CORRECTION

PATENT NO. : 5,353,807
DATED : October 11, 1994
INVENTOR(S) : Thomas J. DeMarco

Page 1 of 2

It is certified that error appears in the above-indentified patent and that said Letters Patent is hereby corrected as shown below:

Column 2, line 17, after "these" insert --conventional endoscope to limit its use and thus its effectiveness to the lower end of the large intestine nearest to the rectum, known as the descending colon. An estimated 20 million Americans have colon polyps. Over 150,000 cases of colon cancer are diagnosed each year and this figure is rising. Therefore, there is a great need in the art for a device which may be intubated into the rectum to allow visualization of the entire colon, without causing great discomfort to the patient, which is easily guidable through the intestine and which is capable of performing a variety of therapeutic and diagnostic medical procedures. Such a device should be easy to master by the non-specialist in primary care or technician so as to make colon cancer screening available to a larger number of people.

There have been prior attempts to provide a device which is capable of magnetically guiding a catheter or similar intubated item within a body. Examples of these attempts include U.S. Patent Nos. 3,961,632, issued to Moosun; 4,077,412, issued to Moosun; 4,249,536, issued to Vega; 4,809,713, issued to Grayzel; 4,671,287, issued to Fiddian-Green; 3,674,014, issued to Tillander; 4,063,561, issued to McKenna; and 4,244,362, issued to Anderson.

UNITED STATES PATENT AND TRADEMARK OFFICE
CERTIFICATE OF CORRECTION

PATENT NO. : 5,353,807  
DATED : October 11, 1994  
INVENTOR(S) : Thomas J. DeMarco Page 2 of 2

It is certified that error appears in the above-indentified patent and that said Letters Patent is hereby corrected as shown below:

However, none of these prior attempts is directed to providing a magnetically guidable intubation device for diagnostic or therapeutic use within the large intestine. Also, these prior attempts are extremely limited in practical use, and--;

Column 2, line 42, delete "conventional";

Delete Column 2, line 43 - line 67;

Delete Column 3, line 1 - line 2;

Column 3, line 3, delete "tical use, and".

Signed and Sealed this

Tenth Day of January, 1995

Attest:

BRUCE LEHMAN

Attesting Officer

Commissioner of Patents and Trademarks